US010487340B2

(12) United States Patent
Liu et al.

(10) Patent No.: US 10,487,340 B2
(45) Date of Patent: Nov. 26, 2019

(54) TOBACCO MOSAIC VIRUS RESISTANT N'AU GENE AND CLONING METHODS AND APPLICATIONS THEREOF

(71) Applicant: Yunnan Academy of Tobacco Agricultural Sciences, Kunming, Yunnan (CN)

(72) Inventors: Yong Liu, Yunnan (CN); Xinjie Yuan, Hubei (CN); Changjun Huang, Yunnan (CN); Yongping Li, Yunnan (CN); Haiqin Yu, Yunnan (CN); Xuejun Chen, Yunnan (CN); Bingguang Xiao, Yunnan (CN)

(73) Assignee: Yunnan Academy of Tobacco Agricultural Sciences, Kunming, Yunnan (CN)

( * ) Notice: Subject to any disclaimer, the term of this patent is extended or adjusted under 35 U.S.C. 154(b) by 0 days.

(21) Appl. No.: 15/545,946

(22) PCT Filed: Oct. 9, 2015

(86) PCT No.: PCT/CN2015/091560
§ 371 (c)(1),
(2) Date: Jul. 24, 2017

(87) PCT Pub. No.: WO2017/059582
PCT Pub. Date: Apr. 13, 2017

(65) Prior Publication Data

US 2018/0016595 A1 Jan. 18, 2018

(51) Int. Cl.

| | |
|---|---|
| ***C12N 15/82*** | (2006.01) |
| ***C07K 14/415*** | (2006.01) |
| ***A01H 1/04*** | (2006.01) |
| ***A24B 15/12*** | (2006.01) |
| ***C12N 15/09*** | (2006.01) |
| *A01H 5/00* | (2018.01) |

(52) U.S. Cl.
CPC .......... *C12N 15/8283* (2013.01); *A01H 1/04* (2013.01); *A24B 15/12* (2013.01); *C07K 14/415* (2013.01); *C12N 15/09* (2013.01); *A01H 5/00* (2013.01)

(58) Field of Classification Search
None
See application file for complete search history.

(56) References Cited

FOREIGN PATENT DOCUMENTS

CN 1157549 A 8/1997

OTHER PUBLICATIONS

International Search Report and Written Opinion dated Jul. 14, 2016 for Application No. PCT/CN2015/091560.
Genbank Submission; NIH/NCBI, Accession No. AB669000. Sekine et al., Sep. 3, 2013. 3 pages.
Genbank Submission; NIH/NCBI, Accession No. BAM17521. Sekine et al., Sep. 3, 2013. 3 pages.
Zhang et al., Tobacco N Gene and Its Application in Genetic Breeding. Chin. Agr. Sci. Bull. Jul. 31, 2013; 29(19): 89-92.
Laskowska et al., Cytology and fertility of viable hybrids of *Nicotiana tabacum* L. cv. TB-566 with N. alata Link et Otto. J Appl Genet. 2005;46(1):11-8.
Nikova et al., *Nicotiana tabacum* L. as a source of cytoplasmic male sterility in interspecific cross with N. alata Link & Otto. Euphytica. 1999;107:9-12.

*Primary Examiner* — Elizabeth F McElwain
(74) *Attorney, Agent, or Firm* — Wolf, Greenfield & Sacks, P.C.

(57) ABSTRACT

The invention relates to the isolation and the cloning and breeding application of a tobacco mosaic virus (TMV) resistant N'au gene. The invention discloses the nucleotide sequence of the TMV resistant N'au gene shown as SEQ ID NO.1. The amino acids of polypeptide encoded by the TMV resistant N'au gene are shown as SEQ ID NO.2. A non-transgenic TMV resistant tobacco variety can be obtained by transferring an N'au gene which is contained by germplasm resources into a TMV infected popular tobacco variety by conventional breeding means. The N'au gene of the invention has a homologous sequence with high identity rate of nucleotides in the popular tobacco variety, so that it is easy to obtain a shorter introgression segment single plant carrying the N'au gene by conventional breeding, and thereby to obtain a TMV resistant variety with lower linkage drag. The gene can resist both U1 strain and Cg strain of TMV. The novel antiviral gene N'au of the invention has great application prospect in cultivation of a TMV resistant tobacco.

4 Claims, 3 Drawing Sheets

Specification includes a Sequence Listing.

TOBACCO MOSAIC VIRUS RESISTANT N'AU GENE AND CLONING METHODS AND APPLICATIONS THEREOF

CROSS REFERENCE TO RELATED APPLICATIONS

The present application is the National Phase under 35 U.S.C. § 371 of PCT International Application No. PCT/CN2015/091560, filed Oct. 9, 2015, which application is incorporated herein by reference in its entirety.

FIELD OF THE INVENTION

The present invention belongs to the technical field of plant protection, further belongs to the technical field of tobacco virus prevention and treatment, and particularly relates to a tobacco mosaic virus resistant N'au gene and cloning methods and applications thereof.

BACKGROUND OF THE INVENTION

Tobacco mosaic virus (TMV) is an important tobacco disease, and the annual loss caused by it ranks forefront of the list of the top ten tobacco infectious diseases (Zhu Xianchao, 2002). There exist strain differentiations for TMV virus, such as TMV-Cg, TMV-U1 strain and the like, among which the TMV-U1 strain is the major strain of tobacco. Since the main cultivars of flue-cured tobacco such as K326, Yunyan 87 and the like are not resistant to TMV-U1 strain, generally, prevention and treatment measures such as cultivation of virus-free seedlings, chemical control and destruction of diseased plants in the field and the like are mainly taken. These measures have certain effects on controlling the occurrence and prevalence of TMV, but the cases of TMV prevail in a local field occur occasionally, leading to larger economic loss (Zhu Xianchao, 2002). Therefore, planting a TMV resistant variety is still the most fundamental and cost-effective mean for preventing and controlling TMV. The requirements for a disease-resistant variety include high resistance, no yield penalty and no agronomic traits disadvantages.

Currently, the TMV resistance resource of flue-cured tobacco is mainly from wild species of tobacco, *Nicotiana glutinosa*, the resistance of which is controlled by one dominant single gene (N). The N gene is resistant to TMV-U1 strain. N gene was cloned in 1994, which is the first NBS type of disease-resistant gene cloned in plants (Whitham, 1994). The length of the genome sequence of the N gene is 6,656 bp, including 5 exons and 4 introns, and belonging to a TIR-NBS-LRR type of disease-resistant genes. The N gene encodes a structure similar to the *drosophila* Toll protein and the extracellular domain of mammalian interleukin-1 receptor (Toll/interleukin-I receptor, TIR) on the N-terminal of the protein it encodes, and it also encodes a nucleotide-binding-site (NBS) and a leucine-rich repeat (LRR) domain (Whitham, 1994). The disease-resistant mechanism of N gene is that hypersensitive necrotic spots (necrotic spots) occur in the infected spots by virus, and the movement of TMV in a plant is limited by cell hypersensitive response caused by induction. After mediating the hypersensitive reaction, tobacco plants can obtain a systematic resistance, and produce a broad-spectrum resistance to the re-invasion of TMV or other similar pathogens (Whitham, 1994). By means of a series of conventional hybridization and backcrossing, the resistance of N gene is transferred from *Nicotiana glutinosa* into an oriental tobacco firstly, and then transferred into a flue-cured tobacco variety (Bagley, 2002). Transferring the resistance of N gene by using hybridization and breeding is actually transferring the chromosome segment carrying N gene (abbreviated as N introgression segment). Almost all the TMV resistant gene used by the breeding of TMV resistant flue-cured tobacco over the world is N gene. The representative varieties are TMV resistant flue-cured tobacco varieties Coker 176 and Speight H2O carrying N gene introgression segment, which are earlier commercially planted. Due to the linkage drags of lower yield, slower yellowing of the upper leaves, and so on, the flue-cured tobacco varieties carrying N gene could not meet the urgent need for leaf production. The linkage drags present in the chromosome segment derived from *Nicotiana glutinosa* which is closely linked to N gene, the narrow genetic background of the TMV resistant resources, which has been used for breeding, and the limitation of conventional breeding means, result in lacking breakthrough of TMV resistant flue-cured tobaccos breeding. Thus, the screening and identification of new TMV resistant gene in the tobacco germplasm resource bank is of great significance.

In addition, there is an N' gene present in the wild tobacco varieties, and the corresponding avirulence gene is the coat protein (abbreviated as CP) gene of the virus of tobacco mosaic virus, belonging to CC-NBS-LRR type of disease-resistant genes (Sekine et al., 2012). N' gene is resistant to TMV-Cg strain but not resistant to TMV-U1 strain.

For this, the present invention is intended to seek for a new gene resistant to TMV virus.

DISCLOSURE OF THE INVENTION

The first object of the present invention is to provide a tobacco mosaic virus resistant N'au gene; the second object is to provide a method for cloning the tobacco mosaic virus resistant N'au gene; the third object is to provide a polypeptide encoded by the tobacco mosaic virus resistant N'au gene; the fourth object is to provide an transient expression vector of the tobacco mosaic virus resistant N'au gene; the fifth object is to provide a method for constructing the transient expression vector of the tobacco mosaic virus resistant N'au gene; the sixth object is to provide applications of the tobacco mosaic virus resistant N'au gene; the seventh object is to provide a tobacco variety, a seed and an asexual propagule thereof obtained according to the applications of the tobacco mosaic virus resistant N'au gene; the eighth object is to provide an expression cassette comprising the tobacco mosaic virus resistant N'au gene; the ninth object is to provide a transgenic cell line comprising the tobacco mosaic virus resistant N'au gene; and the tenth object is to provide a recombinant strain comprising the tobacco mosaic virus resistant N'au gene.

The first object of the present invention is thus achieved with the base sequence of the tobacco mosaic virus resistant N'au gene as shown in SEQ ID No.1.

The second object of the present invention is thus achieved with the method for cloning the tobacco mosaic virus resistant N'au gene comprising the following steps:

(1) using a total DNA of *Nicotiana alata* as a template for PCR amplification, wherein the upstream and downstream primers used are as follows:

```
N'-H8-F:
                                   (SEQ ID NO. 3)
5'-ATGGAGATTGGCTTAGCAGT-3',
and
N'-H8-R:
                                   (SEQ ID NO. 4)
5'-TCACAGGCATTCACAATCGA-3'
```

respectively;

(2) recovering and purifying the resulting PCR product; and (3) sequencing.

The third object of the present invention is thus achieved with the amino acid sequence of the polypeptide encoded by the tobacco mosaic virus resistant N'au gene as shown in SEQ ID No.2.

The fourth object of the present invention is thus achieved with the transient expression vector of the tobacco mosaic virus resistant N'au gene comprising N'au gene and vector pHellsgate 8.

The fifth object of the present invention is thus achieved with the method for constructing the transient expression vector of the tobacco mosaic virus resistant N'au gene being such that the vector pHellsgate 8 is digested by using restriction enzymes XhoI and XbaI, and the PCR amplification product of N'au recovered from gel is connected to the linear pHellsgate 8 vector by using a one-step seamless cloning kit.

The sixth object of the present invention is thus achieved with the application of the tobacco mosaic virus resistant N'au gene being such that a tobacco plant comprising N'au gene is obtained by a chromosome fragment introgression, or a gene introduction, or gene editing.

The seventh object of the present invention is thus achieved with the tobacco variety, seed and the asexual propagule thereof obtained according to the applications of the tobacco mosaic virus resistant N'au gene.

The eighth object of the present invention is thus achieved with the expression cassette comprising the tobacco mosaic virus resistant N'au gene.

The ninth object of the present invention is thus achieved with the transgenic cell line comprising the tobacco mosaic virus resistant N'au gene.

The tenth object of the present invention is thus achieved with the recombinant strain comprising the tobacco mosaic virus resistant N'au gene.

The N'au gene with resistance to both TMV-U1 and TMV-Cg strains provided by the present invention is of great application value. A tobacco variety with broad-spectrum resistance is cultivated by hybridization breeding, transgene, gene mutation and other means. A TMV resistant variety carrying N'au gene and having less linkage drag is easy to obtain by conventional breeding. Studies have found that there is highly homologous sequence of N'au gene in tobacco cultivated varieties such as Yunyan87 and the like, the introgression segment carrying N'au gene is prone to exchange with cultivars, and it is easy to obtain a single plantlet with shorter introgression segment carrying N'au gene. Therefore, a TMV resistant variety carrying N'au gene and having less linkage drag is easy to obtain by conventional breeding. In contrast, since the introgression segment of the wild tobacco variety *Nicotiana glutinosa* carrying N gene are longer, and the nucleotide homology with cultivated tobacco varieties, such as Yunyan87, is lower, the exchange of the introgression segment carrying N gene with cultivated varieties is difficult. A single strain with shorter introgression segment is difficult to obtain by conventional breeding. Therefore, it is difficult to obtain a TMV resistant variety carrying N gene and having less linkage drag.

EMBODIMENTS OF THE INVENTION

Figure 1:
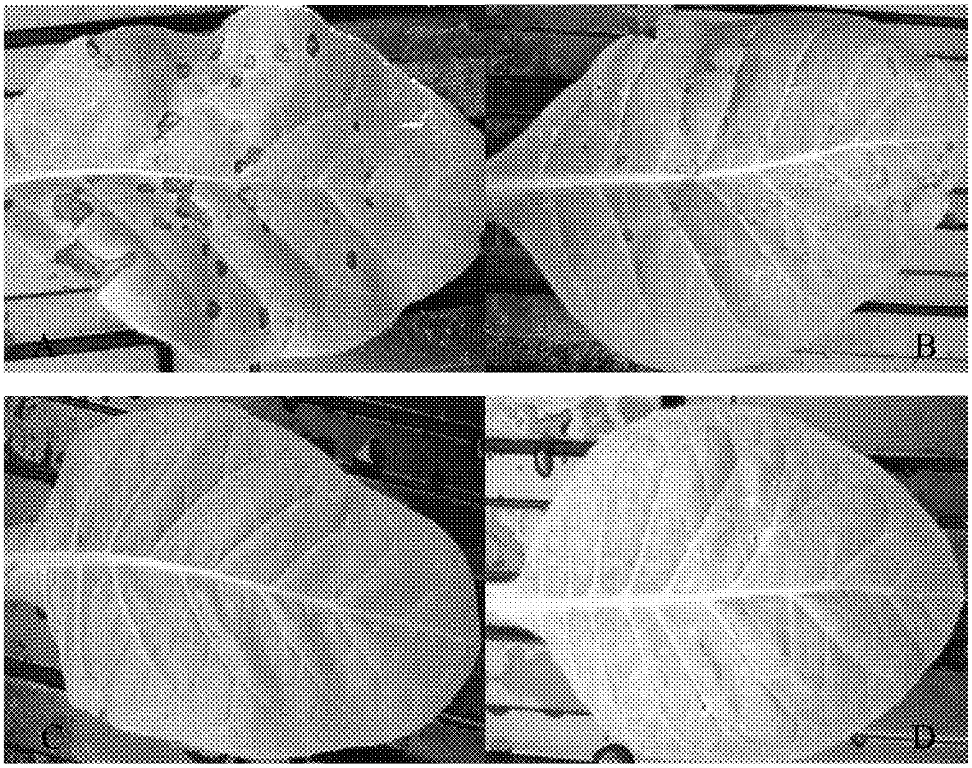
FIG. 1 is the results of 4 tobacco varieties inoculated with TMV-U1 strain virus; in this figure, A is *N. alata* (PI42334), showing necrotic spots; B is Coker176, showing necrotic spots; C is *N. sylverstris* (PI555569), showing mosaic without necrotic spots; and D is K326, showing vein-clear, mosaic without necrotic spots.

A further illustration of the present invention will be described below in conjunction with the accompanying drawings; however, it's not intended to limit the present invention in any manner. Any change made based on the teachings of the present invention would fall within the protection scope of the present invention.

The base sequence of the tobacco mosaic virus resistant N'au gene of the present invention is shown as SEQ ID No.1. The N'au gene is a CC-NBS-LRR gene, not only resistant to TMV-U1 strain of tobacco mosaic virus, but also resistant to TMV-Cg strain.

According to the nucleotide sequence information shown as SEQ ID No.1 provided by the present invention, those skilled in the art can easily obtain a functionally equivalent gene by the following method: (1) by a genomic database search; (2) by screening the genomic library or cDNA library of tobacco with SEQ ID NO.1 as a probe; (3) by PCR amplification method from the genomic library or cDNA library of tobacco with oligonucleotide primers designed according to the sequence information of SEQ ID NO.1; (4) by modification via gene editing method on the basis of the sequence of N' gene; (5) by a chemical synthesis method;

and (6) by a deletion of codons of one or several amino acid residues and/or a mutation of one or several base pairs.

In addition, there may exist variants in nature having significant sequence identity with the polynucleotide as shown in SEQ ID NO.1 or the polypeptide as shown in SEQ ID NO.2 of the present invention. These variants may exist naturally, or may be artificially produced. Compared with the sequence as shown in SEQ ID NO.1, one or more nucleotides are deleted and/or added and/or substituted at one or more sites within the naturally occurring variants. Due to the degeneracy of genetic code, a conservative variant of polynucleotides also includes those sequences encoding the amino acid sequence of the polypeptide as shown in SEQ ID NO.2. The naturally occurring variants could be identified by the well-known molecular biology techniques, for example, by polymerase chain reaction (PCR) and hybridization technique known in the art. The variants produced artificially further include polynucleotides from the synthetic resources, such as a polynucleotide variant produced by site-directed mutagenesis, which still shares significant sequence identity with the naturally occurring sequence disclosed herein. As a result the resistance to the TMV-U1 strain is acquired. Typically, these variants have an identity rate of more than 95% with the sequence shown in SEQ ID NO.1.

The polynucleotide variant can also be evaluated by comparing the sequence shown as SEQ ID NO.2 with the amino acid sequence of the polypeptide encoded by the variant. The sequence identity rate between any two polypeptides could be calculated by sequence alignment programs and parameters. The identity percentage of the consensus sequence of two polypeptides is compared. In general, the sequence identity rate between two polypeptides encoded thereby should be above 95%.

The sequence identity rate may be calculated by using molecular biology methods such as MEGA, BLAST, etc.

In addition, the sequence shown as SEQ ID NO.1 can be isolated from other species of *Nicotiana*. The homology may be identified by PCR, hybridization, and other methods. According to the sequence identity with the nucleotide sequence shown as SEQ ID NO.1, or variants and segments thereof, sequences with the function of TMV-U1 strain resistance are isolated. Such kinds of sequences include an ortholog sequence of the sequence shown as SEQ ID NO.1. "Ortholog" is a gene derived from a common ancestral gene and found in different species as a result of the species formation. It is found in different species that genes which have a sequence identity of more than 95% in the nucleotide sequence thereof and/or the protein encoded thereby are considered as orthologs. The function of orthologs is often highly conservative among species.

The method of cloning the tobacco mosaic virus resistant N'au gene of the present invention comprising following steps:

(1) using a total DNA of *Nicotiana alata* as a template for PCR amplification, wherein the upstream primer and downstream primers used are as follows:

```
N'-H8-F:
                                    (SEQ ID NO. 3)
5'-ATGGAGATTGGCTTAGCAGT-3',
and

N'-H8-R:
                                    (SEQ ID NO. 4)
5'-TCACAGGCATTCACAATCGA-3',
```

respectively;

(2) recovering and purifying the resulting PCR product; and (3) sequencing.

The total volume of the PCR reaction system is 50 μL, containing 4.0 μL of 100 ng/μL DNA sample, 10.0 μL of 5×PCR buffer, 4 μL of dNTPs (2.5 mmol/L each), 2.0 μL of 10 μmol/L primer N'-H8-F and N'-H8-R each, 1 μL of PrimeSTAR GXL DNA Polymerase, and 27 μL of $ddH_2O$. The reaction condition of the PCR is 98° C., 2 min; 38 cycles of 98° C., 10 s, 52° C., 15 s, 68° C., 5 min; and 68° C., 10 min.

The method of the sequencing can be direct sequencing, and can also be the cloning sequencing by TA vector.

The amino acid sequence of the polypeptide encoded by the tobacco mosaic virus resistant N'au gene of the present invention is shown as SEQ ID No.2.

The transient expression vector of the tobacco mosaic virus resistant N'au gene of the present invention comprises N'au gene and vector pHellsgate 8. The method for constructing the transient expression vector is such that the vector pHellsgate 8 is digested by using restriction enzymes XhoI and XbaI, and a PCR amplification product of N'au gene recovered from gel is connected to the linear pHellsgate 8 vector using a one-step seamless cloning kit. As a preferred embodiment of the invention, the one-step seamless cloning kit is One Step Cloning Kit ClonExpress™ II.

An application of the tobacco mosaic virus resistant N'au gene of the present invention is to obtain a tobacco plant comprising N'au gene by a chromosome segment introgression, a gene introduction and/or gene editing. The method of chromosome segment introgression comprises hybridization breeding, protoplasts fusion and/or introgression of chromosome segment into substitution lines or introgression lines to transfer into the target tobacco, thus obtaining a new Tobacco mosaic virus resistant variety. Firstly, a germplasm resource comprising N'au gene is obtained by screening from *Nicotiana* plants, by using a functional molecular marker or a linked molecular marker associated with the sequence shown as SEQ ID NO.1, or by artificial inoculation of TMV; the germplasm resource comprises wild species of cultivated tobacco, a cultivated cultivar of tobacco, and a hybrid cultivar of wild species and a cultivated cultivar of tobacco. Then, such tobacco material having increased-resistance is bred to be a commercial variety to improve the TMV resistance of main tobacco cultivars by hybridization, backcrossing and other breeding means.

The gene introgression relates to introducing an exogenous resistance gene into a target tobacco, including an introduction after the transferring of the exogenous gene (i.e., transgene) and a direct introduction. The most commonly used method for transgene is *Agrobacterium* transformation method. The method of direct introduction includes conventional biological methods such as microscope injection, pollen tube pathway, conductivity, gene gun, and the like to transform tobacco cells or tissues. The transformed tissues are cultivated into a plant.

Gene editing is a recently developed technique which can accomplish the accurate modification to a genome, which can accomplish site-directed InDel mutation, knock-in, simultaneous mutation on multiple sites, and deletion of small segments of gene, etc., and can perform accurate gene editing at genomic level. Accurate gene editing performed on the homologue of N'au gene allows the edited homologue to obtain the function of resistance to TMV-U1 and TMV-Cg strain.

A new TMV resistant tobacco variety, seeds and asexual propagules thereof can be obtained, depending on the application of the tobacco mosaic virus resistant N'au gene. In addition, some genetic engineering products including an expression cassette, a transgenic cell line and a recombinant strain, etc., of the resistant tobacco mosaic virus can also be developed.

Further explanation and verification will be given below in combination with examples.

Unless otherwise specified, the methods used in the following examples were all conventional methods. If there is no special specification, the experimental materials used were all purchased from conventional biochemical reagent companies. The tobacco materials were *N. sylverstris* (PI555569), *N. alata* (PI42334), *N. benthamiana*, Coker176, and K326, which are all from Yunnan Tobacco Agricultural Science Research Institute. TMV-U1 and TMV-Cg strain virus were from Yunnan Tobacco Agricultural Science Research Institute. The cDNA of TMV-U1 and TMV-Cg were obtained by a conventional method of the reverse transcription of total RNA extracted from virus-infected tobacco leaves by conventional methods.

Gateway LR clonase Enzyme Mix kit and pENTR2B vector were purchased from Invitrogen Corporation, and *Agrobacterium* GV3101 was purchased from Invitrogen Corporation. The pHellsgate8 vector was purchased from Thermofisher Company. Plasmid DNA extraction kit, Agarose gel DNA recovery kit, and DNA fragment purification kit were purchased from QIAGEN Company. *Escherichia coli* DH5a, restriction enzymes, reverse transcription kit, DNA Marker, PrimeSTAR GXL DNA Polymerase, T4 DNA polymerase and T4 DNA ligase, and spectinomycin were all purchased from Takara (Dalian) Company and Roche Company. RNA extraction kit Trizol was purchased from Invitrogen Corporation, and ELISA kits for detecting TMV and Immunostrips were purchased from Agdia Company.

The culture and inoculation method of *Agrobacterium: Agrobacterium tumefaciens* GV3101 was transformed with a transient expression vector plasmid. The positive clones were activated by a shake culture in 2 mL LB antibiotics (50 mg/L rifampicin, and 50 mg/L spectinomycin) medium, at 28° C., at 210 r/min for 30 hours. 150 μL activated bacteria solution was added to 10 mL LB medium (containing 10 mmol/L morpholine ethane sulfonic acid (MES) (pH 5.6), 40 μmol/L acetosyringone, 50 mg/L rifampicin, and 50 mg/L spectinomycin). After cultivated at 28° C., at 210 r/min for 16 hours, the bacteria was collected by a centrifugation at 4700 r/min for 5 minutes. The bacteria was resuspended and adjusted to a bacteria solution with an $OD_{600}$=0.6 by using infiltration buffer (10 mmol/L $MgCl_2$, 10 mmol/L MES, 200 μmol/L acetosyringone). After kept at room temperature for 3 hours, the 4-week old tobacco seedling leaf was infiltrated with a 2 mL syringe. After inoculation, the tobacco seedling was cultivated in a light culturing room at 25~28° C. for 7 days and the hypersensitive response (HR reaction) was surveyed and observed.

Example 1: Discovery and Function Verification of TMV-U1 Strain Resistant N'Au Gene of *N. alata* (PI42334)

(1) TMV-U1 Strain Resistant *N. alata* (PI42334), with a Resistance Different from N Gene 15 plants for each of the four kinds of tobaccos variety such as *N. sylverstris* (PI555569), *N. alata* (PI42334), Coker176, and K326 were planted (potted). When there were 4-5 leaves, each was inoculated with TMV-U1 strain and a blank control. The symptoms on the $5^{th}$, $7^{th}$ and $14^{th}$ day after inoculation were surveyed and recorded.

The result on $7^{th}$ day after inoculation of virus shows that *N. alata* (PI42334) and Coker176 are TMV-U1 strain resistant, and *N. sylverstris* and K326 are susceptible to TMV-U1 strain (Table 1, FIG. 1). This suggests that there is a disease-resistant gene against TMV-U1 strain in *N. alata* (PI42334) and Coker176.

TABLE 1

Results of four kinds of tobacco varieties inoculated with TMV-U1 strain

| Tobacco variety | TMV-U1 strain | Blank control | Detection of N1N2 marker | Detection of E1E2 marker |
|---|---|---|---|---|
| *N. alata* (PI42334) | HR | No symptom | Negative | Negative |
| Coker176 | HR | No symptom | Positive | Positive |
| *N. sylverstris* (PI555569) | mosaic | No symptom | Negative | Negative |
| K326 | mosaic | No symptom | Negative | Negative |

Notes:
HR is the disease-resistant reaction; and mosaic is an infected symptom.

Figure 2:
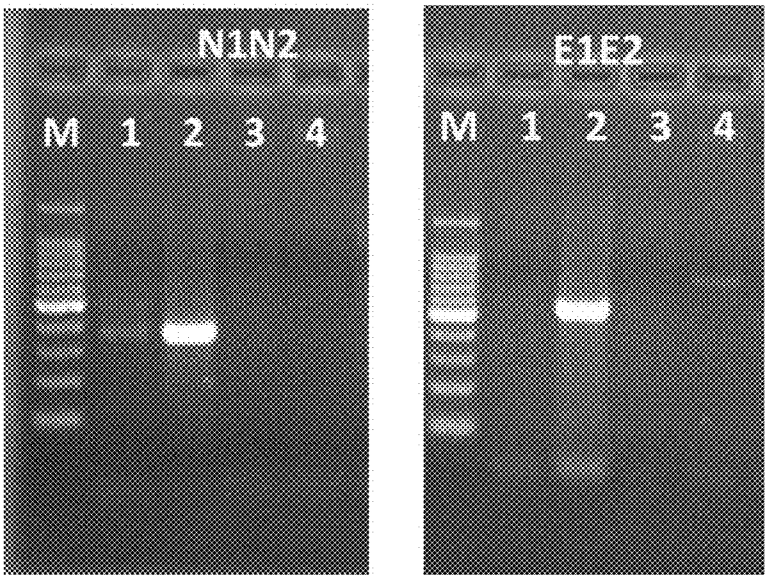
FIG. 2 is the results of detecting N gene by using molecular markers N1/N2 and E1/E2; in this figure, 1 is *N. alata* (PI42334); 2 is Coker176; 3 is *N. sylverstris* (PI555569); 4 is K326; and M is a molecular weight standard of 2000 bp.

It has been reported in the literature that there is a TMV-U1 strain resistant N gene in Coker176, and specific molecular markers N1/N2 and E1/E2 for detecting N gene have been developed (Lewis, 2005). In order to verify the relationship between the disease-resistant genes in *N. alata* (PI42334) and N gene, leaves from the four kinds of tobacco varieties were taken, the DNA from each was extracted by QIAGEN kit, and PCR detection was performed by using specific molecular markers N1/N2 and E1/E2 of N gene. The result (Table 1, FIG. 2) shows that the test results of all the 3 kinds of tobacco varieties are negative except Coker176. It suggests that TMV-U1 strain resistant gene of *N. alata* (PI42334) is not N gene, and there is a new resistant gene resistant to TMV-U1 strain in *N. alata* (PI42334), named N'au gene.

(2) Confirmation of TMV-U1 Resistant Avirulence Gene of *N. alata* (PI42334)

Construction of a transient expression vector of TMV-U1 and TMV-Cg CP gene: transient expression vectors of coat proteins (abbreviated as CP) gene of TMV-U1 and TMV-Cg strain were constructed by using a modified vector pHellsgate8. The following primer pairs were used to amplify the viral cDNA of the CP genes of TMV-U1 and TMV-Cg strain:

```
U1-CP-F:
                                       (SEQ ID NO. 5)
5'-AAAAAGCAGGCTATGTCTTACAGTATCACTACTCCATCTC-3';

U1-CP-R:
                                       (SEQ ID NO. 6)
5'-AGAAAGCTGGGTTCAAGTTGCAGGACCAGAGG-3';

Cg-CP-F:
                                       (SEQ ID NO. 7)
5'-AAAAAGCAGGCTATGTCTTACAACATCACGAGCTCG-3';
and

Cg-CP-R:
                                       (SEQ ID NO. 8)
5'-AGAAAGCTGGGTCTATGTAGCTGGCGCAGTAGTCC-3'.
```

The amplified fragment is inserted into pHellsgate8 vector according to the method of pHellsgate8 vector kit protocol. The attB sites are amplified by using the following primer pairs:

```
attB1_adapter:
                                        (SEQ ID NO. 9)
5'-GGGGACAAGTTTGTACAAAAAAGCAGGCT-3';
and

attB2_adapter:
                                        (SEQ ID NO. 10)
5'-GGGGACCACTTTGTACAAGAAAGCTGGGT-3'.
```

The amplified fragment is inserted into pDONR221 vector (Invitrogen) according to the method of pDONR221 vector (Invitrogen) kit for BP reaction protocol, and then inserted into expression vector pHellsgate8 by using LR reaction of Gateway® technique.

To determine the avirulence gene in *N. alata* (PI42334) interacting with TMV-U1 strain, the transient expression vectors *Agrobacterium* of TMV-U1 CP and TMV-Cg CP and a blank vector *Agrobacterium* control were used to inoculate the tobacco with a 2 mL syringe. Before inoculation, a suitable tobacco leaf was uniformly punched with a syringe needle. Five plants for each of the *N. sylverstris* (PI555569), *N. alata* (PI42334), Coker176 and K326 during 4~5 leaves period were infiltrated and inoculated. The largest 2 leaves of each plant were inoculated. The plants were cultivated in dark for 1~2 days after inoculation, and HR reaction was investigated on the $7^{th}$, $10^{th}$ day at 28° C. in a light culturing room.

Figure 3:
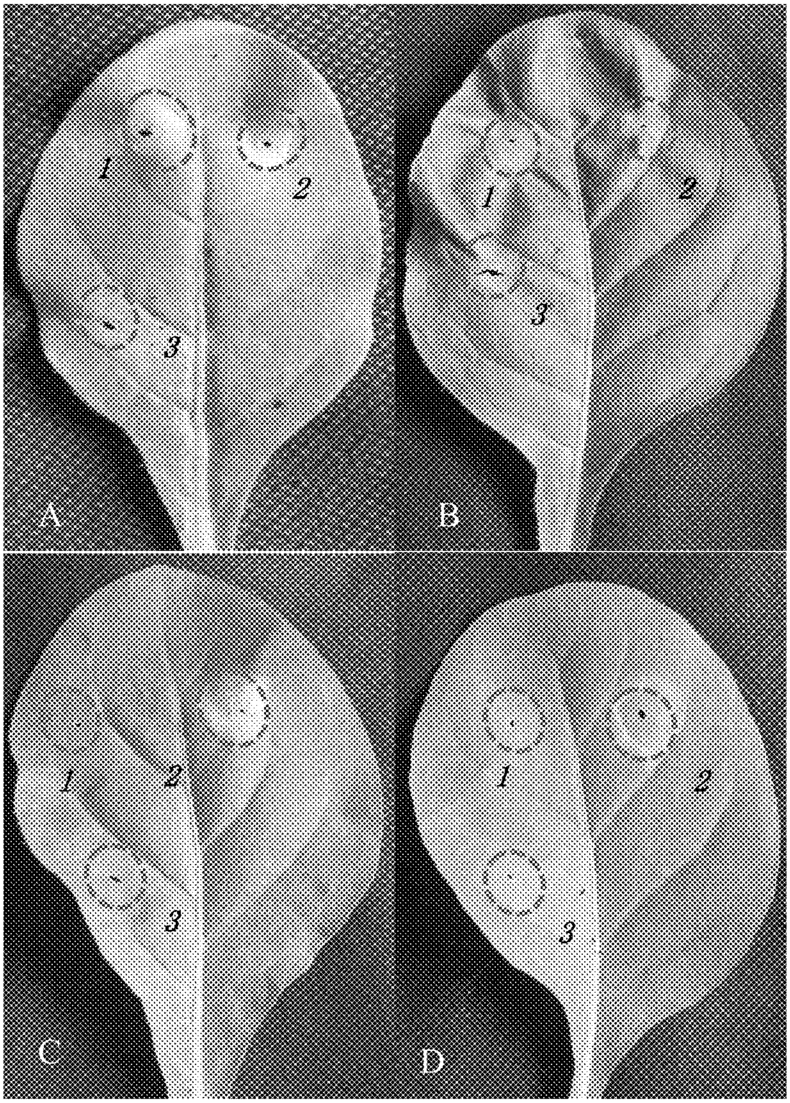
FIG. 3 is the results of 4 tobacco varieties inoculated with a transient expression vector *Agrobacterium* of TMV-U1 CP, TMV-Cg CP and blank, respectively; in this figure, A is *N. alata* (PI42334); B is Coker176; C is *N. sylverstris* (PI555569); D is K326; 1 is inoculated with the transient expression vector *Agrobacterium* of TMV-U1CP; 2 is inoculated with the transient expression vector of TMV-Cg CP; and 3 is inoculated with the transient expression vector *Agrobacterium* of blank.

The result (Table 2, FIG. 3) suggests that the *N. alata* (PI42334) inoculated with *Agrobacterium* of TMV-U1 CP exhibits HR reaction, indicating that the avirulence gene interacting with TMV-U1 strain in *N. alata* (PI42334) is CP. The Coker176 inoculated with *Agrobacterium* transient expression vector of TMV-U1 CP doesn't exhibit HR reaction, indicating that the avirulence gene interacting with TMV-U1 strain in Coker176 is not CP. It further suggests that the TMV-U1 strain disease-resistant gene in *N. alata* (PI42334) is different from the N gene in Coker176. The *N. alata* (PI42334), *N. sylverstris* (PI555569) and K326 inoculated with *Agrobacterium* of TMV-Cg CP all exhibit HR reaction, indicating that there is a disease-resistant gene interacting with TMV-Cg CP in the three tobacco materials, and the HR reaction in the Coker176 inoculated with *Agrobacterium* of TMV-Cg CP is not typical. According to the existing literatures, the disease-resistant gene interacting with tobamovirus CP in *N. sylverstris* (PI555569) is N' (Sekine, 2012), and there is also an N' gene in K326. The test result suggests that there is indeed a new gene in *N. alata* (PI42334) whose gene function is different from that of N' gene in *N. sylverstris* (PI555569).

TABLE 2

Avirulence gene interacting with TMV-U1 strain in *N. alata* (PI42334)

| Tobacco variety | TMV-U1 CP (number of leaves exhibiting HR/ number of leaves inoculated) | TMV-Cg CP (number of leaves exhibiting HR/ number of leaves inoculated) | Blank vector BLK (number of leaves exhibiting HR/ number of leaves inoculated) |
|---|---|---|---|
| *N. alata* (PI42334) | 10/10 | 10/10 | 0/10 |
| Coker176 | 0/10 | 0/10 | 0/10 |
| *N. sylverstris* (PI555569) | 0/10 | 10/10 | 0/10 |
| K326 | 0/10 | 6/10 | 0/10 |

Example 2: Cloning and Sequence Analysis of the N'Au Gene of *N. alata* (PI42334)

(1) Extraction of the total DNA of tobacco: a fresh tobacco leaf was taken, and the total genomic DNA of tobacco was extracted by using QIAGEN DNeasy Plant Mini kit. DNA quality was preliminarily detected by using UV spectrophotometry (Nanodrop) and Agarose gel electrophoresis method. DNA samples with acceptable quality were diluted to 100 ng/μL by using 0.5×TE solution, and preserved until ready for use.

(2) Cloning of N'au gene: PCR amplification was performed by using the DNA of *N. alata* (PI42334) or *N. sylvestris* (PI555569) as a template, and using primer N'-H8-F (5'-ATGGAGATTGGCTTAGCAGT-3' (SEQ ID NO.3)) and primer N'-H8-R (5'-TCACAGGCATTCACAATCGA-3' (SEQ ID NO.4)). The total volume of PCR reaction system is 50 μL, containing 4.0 μL of 100 ng/μL DNA sample, 10.0 μL of 5×PCR buffer, 4 μL of dNTPs (2.5 mmol/L each), 2.0 μL of 10 μmol/L primer N'-H8-F and N'-H8-R each, 1 μL of PrimeSTAR GXL DNA Polymerase, and 27 μL of $ddH_2O$. The reagents used were purchased from Takara Bio. The reaction condition for PCR is 98° C., 2 min; 38 cycles of 98° C., 10 s, 52° C., 15 s, 68° C., 5 min; and 68° C., 10 min.

Figure 4:
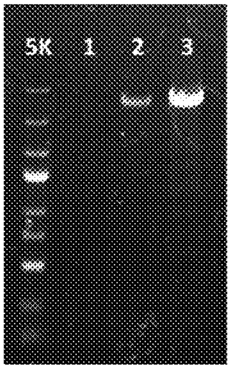
FIG. 4 is the PCR amplification result of N'au gene; in this figure, 1 is $ddH_2O$ (negative control); 2 is *N. sylvestris* DNA (positive control); 3 is *N. alata* (PI42334) DNA; and 5K is a molecular weight standard of 5 kb.

(3) Recovery and purification of PCR product: The PCR product was electrophoresed through 1.5% Agarose gel. The electrophoresis buffer was 1×TAE. When the electrophoresis indicator bromophenol blue migrated sufficiently to separate DNA fragments under the condition of 120V for 60 minutes, the gel was taken down. The result was recorded by using gel image analysis system, as shown in FIG. 4. The gel containing the DNA fragment was cut off under UV lamp. The DNA was recovered by using gel recovery kit (QIAGEN Inc.).

(4) PCR product sequencing: The PCR product from gel recovery was sent to Takara Bio for sequencing. The DNA sequence of N'au gene is shown as SEQ ID No.1 in the sequence list, and the open reading frame is from the Pt to the $4143^{th}$ position at the 5' end of the sequence of SEQ ID No.1 in the sequence list.

Example 3: Polypeptide Sequence Encoded by N'Au Gene

According to the nucleotide sequence of N'au gene, the amino acid sequence of the polypeptide encoded by the N'au gene, which is deduced by using molecular biology software MEGA6, is shown in SEQ ID No.2.

Example 4: Construction of a Transient Expression Vector of N'Au and N' Gene

Vector pHellsgate 8 was digested by using restriction enzymes XhoI and XbaI. The amplification products of N'au and N' recovered from gel were linked to linear vector pHellsgate 8 by using One Step Cloning Kit ClonExpress™ II (Vazyme, Nanjing, China).

Example 5: Verifying that N'Au Gene Possesses the Biological Function of TMV-U1 and TMV-Cg Resistance To determine that the N'au gene in *N. alata* (PI42334) has the biological function of TMV-U1 and TMV-Cg resistance, the *Agrobacterium* transient expression vector of N'au and N' were constructed. The construction of transient expression vector of N'au was the same as that in Example 4, and the construction of the transient expression vector of N' was the same as that in Example 4.

After the accomplishment of construction, a combination of the following transient expression vectors was infiltrated and inoculated by using *Agrobacterium*: N'au+U1 CP; N'au+CgCP; N'au+BLK. N'+U1CP; N'+CgCP; N'+BLK, wherein BLK is a blank transient expression vector. *N. benthamiana*, a wild tobacco variety was infiltrated and inoculated. 10 plants of *N. benthamiana* were inoculated during 4~5 leaves period, and the largest 2 leaves of each plant were inoculated. The HR reaction was investigated on the $7^{th}$ and the $10^{th}$ day.

Figure 5:
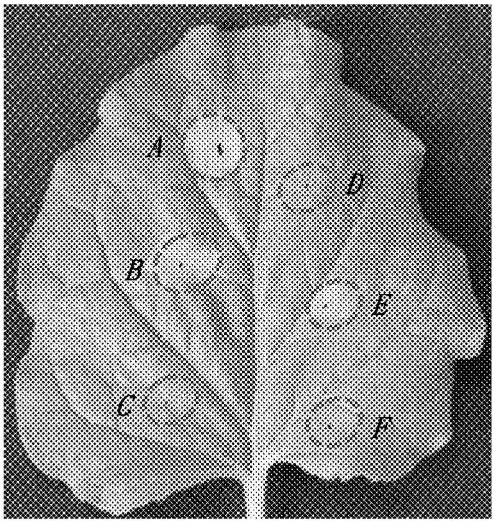
FIG. 5 is an *N. benthamiana* inoculated with the transient expression vector *Agrobacterium* comprising N'au and N' gene. In this figure, A is inoculated with the transient expression vector *Agrobacterium* of N'au+TMV-U1CP; B is inoculated with the transient expression vector *Agrobacterium* of N'au+TMV-Cg CP; C is inoculated with the transient expression vector *Agrobacterium* of N'au+BLK; D is inoculated with the transient expression vector *Agrobacterium* of N'+TMV-U1 CP; E is inoculated with the transient expression vector *Agrobacterium* of N'+TMV-Cg CP; F is inoculated with the transient expression vector *Agrobacterium* of a combination of N'+BLK(F).

The result suggests that (Table 3, FIG. 5) HR reaction occurred on *N. benthamiana* when N'au was infiltrated simultaneously with TMV-U1 CP and TMV-Cg CP, while no HR reaction occurred on *N. benthamiana* when N' was co-infiltrated with TMV-U1 CP. This indicates that N'au has the biological function of TMV-U1 and TMV-Cg strain resistance, and N' does not have the biological function of TMV-U1 strain resistance. N'au and N' have significant difference on the biological function of TMV-U1 strain resistance.

TABLE 3

Infiltration with N'au in combination with TMV-U1CP and TMV-CgCP results in HR reaction.

| Gene | TMV-U1 CP (number of HR leaves/number of total leaves) | TMV-Cg CP (number of HR leaves/number of total leaves) | Blank vector (BLK) (number of HR leaves/number of total leaves) |
|---|---|---|---|
| N'au | 20/20 | 20/20 | 0/20 |
| N' | 0/20 | 9/20 | 0/20 |

Example 6: Conventional Breeding Application of N'Au Gene

The chromosome segments comprising N'au gene shown as SEQ ID NO.1 in *Nicotiana* plants were transferred into the target tobacco by conventional breeding method. By using a functional molecular marker or a linked molecular marker of N'au, or method of artificial inoculation of TMV, the germplasm resource comprising N'au gene was obtained by screening from *Nicotiana* plants. The germplasm resource comprises wild species of cultivated tobacco, a hybrid cultivar of wild species and a cultivated cultivar of tobacco, and a cultivated cultivar of tobacco. The chromosome segments comprising N'au gene in the germplasm resource were introduced into the target tobacco to obtain the non-transgenic tobacco materials with increased TMV resistance by using conventional crossbreeding or protoplast fusion or introduction of chromosome segments or other technical means. Such resistance-increased tobacco materials were bred to be a commercial variety to improve the TMV resistance in a main cultivated variety by hybridization, backcrossing and other breeding means.

Example 7: Breeding Application of Gene Editing of N'Au Gene

The homologue of N'au gene in the target tobacco acquired a function equivalent to N'au by biotechnology modification. Tobacco with increased resistance was obtained. The homologue of N'au gene in the target tobacco was obtained by cloning. The nucleotide sequence and amino acid sequence of the homologue of N'au gene were obtained by sequencing. The difference between the homologue of N'au gene and the N'au in the nucleotide and amino acid sequence was found by sequence alignment analysis. The key different nucleotides which determine that the N'au is TMV-U1 strain resistant while the homology of N'au gene is TMV-U1 strain susceptible were found by means such as PCR mutation, and inoculation by co-infiltrating with TMV-U1 CP *Agrobacterium* transient expression vector, etc. By using molecular biology techniques such as mutagenesis, gene editing and the like, the key different nucleotides of the homologue of N'au gene were modified to be the polynucleotide sequence corresponding to N'au gene, such that the modified homologue of N'au gene acquires the function of TMV-U1 strain resistance.

In summary, N'au gene is a new disease-resistant gene which is not only different from N gene, but also different from N' gene, and it can be both TMV-U1 strain resistant and TMV-Cg strain resistant. Thus, there is broad application prospect in actual production.

REFERENCES

Zhu Xianchao, Wang Yanting, Wang Zhifa. 2002. *Chinese tobacco diseases. Beijing: China Agriculture Press,* 152-162.

Bagley C A. 2002. *Controlling tobacco mosaic virus in tobacco through resistance*. M. S. thesis. Virginia Polytechnic Inst. and State Univ., Blacksburg, Va.

Lewis R S, Milla S R, Levin J S. 2005. *MolecuLar and genetic characterization of Nicotianaglutinosa L. chromosome segments in tobacco mosaic virus-resistant tobacco accessions*. CropSci, 45: 2355-2362.

Whitham S, Dinesh-Kumar S P, Choi D, et al. 1994. *The product of the tobacco mosaic virus resistance gene N: Similarity to Toll and the Interleukin-*1 *receptor*. Cell, 78: 1101-1115.

Sekine K T, Tomita R, Takeuchi S, et al. 2012. *Functional differentiation in the leucine-rich repeat domains of closely related plant virus-resistance proteins that recognize common avr proteins*. Mol Plant Microbe Interact., 25(9):1219-1229.

The invention claimed is:

1. A method for producing a tobacco plant resistant to a tobacco mosaic virus, comprising introducing a tobacco mosaic virus resistant N'au gene as shown in SEQ ID NO: 1 into a tobacco plant by a chromosome segment introgression, a gene introduction and/or gene editing.

2. The method according to claim 1, wherein the chromosome segment introgression includes: transferring a chromosome segment comprising the N'au gene to the tobacco plant by hybridization breeding, protoplast fusion and/or introgression of the chromosome segment into substitution lines or introgression lines.

3. The method according to claim 1, wherein the gene introduction includes: introducing the N'au gene to the tobacco plant.

4. A tobacco variety, a seed and an asexual propagule thereof obtained by the method according to claim 1.

* * * * *

SEQUENCE LISTING

```
<160> NUMBER OF SEQ ID NOS: 10

<210> SEQ ID NO 1
<211> LENGTH: 4143
<212> TYPE: DNA
<213> ORGANISM: Nicotiana alata

<400> SEQUENCE: 1

atggagattg gcttagcagt tggaggtgca tttctatctt cagctttgaa tgttctcttt      60

gataggcttg ctcctcaggg cgagctgctc aagatgtttc agagggacaa acatgatgtt     120
```

-continued

```
cgattattaa agaagctgag aattaccttg cttggtcttc aggctgtact atgtgatgca    180
gagaataaga aggcatcaaa tcaatacgtg agccagtggc ttaatgagct tcaagatgct    240
gtggacagtg ctgaaaactt aatggaagaa atcaattatg aagttctgag acttaaggtg    300
gaaggtcagt atcaaaatct tggagaaaca agcaaccagc aagtaagtga cctcaacttg    360
tgcttgagtg atgaattttt ccttaacata aaggacaagt tggaagacgc cattgaaata    420
ttggaggagt tggaaaagca aatcggtcgc cttgatctaa caaagtatct tgattcagat    480
aaacaagaaa ctagaagact ttcaacttct gtggttgatg actctgatat ctttggcagg    540
cagaatgaaa tagaggaatt ggtgggccgt ttattatctg ttgctgtaaa tggcaaaaat    600
ttgacagtaa ttcctattgt tggaatggct gggattggca agacaacact tgctaaagtt    660
gtttacaatg atgagaaggt gaaagaccat tttgatttga aagcttggtt ttgtgtgtct    720
gaaccatatg atgctttcag aataacaaaa gggttacttc aagaaatagg ctcatttgac    780
ttaaagatgg ataacaatct taatcagcta caagtcaaat tgaaggaaag cttaaagggc    840
aaaaaatttc ttattgttct ggatgatgtt tggaatgaca actataatgc atgggatgac    900
ttgaaaaatc tttttgttca aggaaatgca ggaagtacga tcattgtgac gacacgtaag    960
aaaagtgttg ccaagacgat gggtaatgag caaattagca tggatacttt gtctagtgat   1020
gtctcttggt ctttattcaa aagacatgca tttgacaaca tggatcctaa ggagcatcca   1080
gaacatgtag aagttgggaa agaaatcgta gctaagtgca aaggactgcc tttagctctg   1140
aagacgcttg ctggcatttt acgttccaaa tcagagattg aagggtggaa acgtattttg   1200
agaagtgaag tatgggagct gccagacaat ggcatattac cagcattgat gttgagctac   1260
aacgatcttc ctgcacattt aaagcaatgt ttttcctact gtgcaatatt tccgaaagat   1320
tatccatttc ggaaaaaaca agtcattcag ttgtggattg ccaatggtct agtacagggg   1380
ttgcaaaaat atgaaacaat tgaagattta ggcaacctat tctttctcga gttgcaatca   1440
aggtcacttt tcgaaagggt cccagagtct tctaaaaata atgcagagaa attcttaatg   1500
catgaccttg tcaatgattt ggcccaagtt gcatcttcaa aactttgtgt taggttggaa   1560
gagtaccaag agtctcatat gttgaaaaga agtcgacaca tgtcctattc aatgggctat   1620
gctgactttg aaaagttgca acctctctac aaattggagc agctcaggac attgcttcca   1680
atatacaata tcgagctata tggttcttct ctaagcaaga gggtgttgct taacatattg   1740
ccaagattaa catccttaag ggcactatca ttgtctcgtt ataatatcaa ggagttacca   1800
gatgtcttgt ttatcaaatt aaaactccta agattggtgg acctttcttt gacgcagata   1860
atacagttac cggattcaat ttgtgtgctc tataacttgg agatacttct cttgtcatct   1920
tgtgaatttc ttaaagagtt accgaggcag atggagaagt tgataaactt gcgtcacctt   1980
gacattagcg gcagttctcg cttgatgatg ccgctacatt tgagcaagtt gaaaagcctt   2040
catgtgttat tgggagctga atttcttgta ggtgatcgga gtggttcgag aatggaagat   2100
ttgggtgaac tatgcaactt gtatggaact ctatcaattc gacagttgga aaatgtggcg   2160
gatagaaggg aagctttgaa ggcaaacata agaggaaagg agcatattga gaagttatta   2220
ttggagtgga ctgtaagtat tgcggacagt tcacaaaatg aaagagacat acttggtgag   2280
gtacatccaa atccaaacat aaaagaactt gcgatcaatg gatatagagg gacaaacttt   2340
ccaaattggc tagctgatta ttcattttct gagctggtgg aattgtctct aagtaattgc   2400
aaggactgtt attccttgcc agcattaggc cagcttcctt ctttgaaatt ccttgcaatt   2460
```

-continued

```
cgagggacgc atcgaataat agaggtgact gaagaatttt atggtagctc gtcctccaaa   2520

aagcctttta attctcttga aaagcttgat tttgcagaga tgttggagtg ggagcagtgg   2580

catgtactag gaaatgggga gttccctgta cttcaacacc tttcaattga agattgcccc   2640

aagttgattg gaaagttgcc tgaaaatctt tgttctctga caaaattgac aatttcacat   2700

tgtccggaac tcaatctgga gacacctgta aaatttccaa gtctaaaaaa gtttgaagtt   2760

gaaggttctc ctaagattgg agttcttttt gatcatgctg aactgttttt gtctcaactt   2820

cagggtatga aacagatagt tgaattatat atcagtgatt gtcactctct tacctccttg   2880

cccattagca gtctgccaaa taccttgaaa gtaataagga taaagcattg tgagaaattg   2940

aaattggagt cgtcagttgg taagatgatt tctagaggaa gtaacatgtt tcttgaaagt   3000

ttggaactgg aagaatgtga ttctatagat gatgtatcac ctgagttggt cccatgtgca   3060

cgctatctga gagtagaaaa ttgtctaagc cttactagac ttattattcc caatggggct   3120

gaagatctca aaattaagaa atgtgagaat cttgaaatac tttcggtggc tcagacgacg   3180

cccttgtgta acttgttaat tagcaactgc gagaagctga agtcgttgcc agaacatatg   3240

caggagctcc ttccatctct tagagatctg tatctggaaa attgttcaga aatagtgtcc   3300

ttttctgaag gaggattgcc cttcaattta gaaatcctcg ggatccagga ttgtggtgaa   3360

ctggtgaata gacgaaagga gtggaattta cagggactcc cctctctcac atatttagac   3420

atcatccatc gcggtttcga aaactgggat attatctgcg agttgccttg ctctattcga   3480

agtcttacca tagacaattt gaaaacattt agcagccaag ttctcaaaag cctcacctct   3540

cttgaatatc tatgtacttc taatttacct caaattcagt tactgttgga agaagggctt   3600

cccacatctc ttttaatgct aacattatct caccatggtg agctccattc cctaccgacc   3660

gacggtcttc ggcgcctcac ttcgcttcaa cgtctacgca tcgataattg ccctaatctc   3720

caatatgttc cagaatcaac gtttccctct tccctctctg agctacatat tagtagctgt   3780

agttttctcc aatcgcttcg agaatcagcg ctgtcctcct ccctctctaa tcttttcatc   3840

tacacttgcc ctaatctcca atctctaatg ctgccctcct ccctctttga gctgcatatc   3900

attgattgcc gtaatctcca atctcttcca gaatcagcgc tgccccccctc cctctctaag   3960

ttaatcatcc ttacatgccc taatctccaa tctcttccag taaaagggat gccctcttcc   4020

atctcttttc tgtctattat tgactgccca ttgctcaaac caagtctaga atttgagaag   4080

ggcgaatact ggccaaatat tgctcatatt cccaccatag tgatcgattg tgaatgcctg   4140

tga                                                                 4143
```

<210> SEQ ID NO 2
<211> LENGTH: 1380
<212> TYPE: PRT
<213> ORGANISM: Nicotiana alata

<400> SEQUENCE: 2

```
Met Glu Ile Gly Leu Ala Val Gly Gly Ala Phe Leu Ser Ser Ala Leu
1               5                   10                  15

Asn Val Leu Phe Asp Arg Leu Ala Pro Gln Gly Glu Leu Leu Lys Met
            20                  25                  30

Phe Gln Arg Asp Lys His Asp Val Arg Leu Leu Lys Lys Leu Arg Ile
        35                  40                  45

Thr Leu Leu Gly Leu Gln Ala Val Leu Cys Asp Ala Glu Asn Lys Lys
    50                  55                  60

Ala Ser Asn Gln Tyr Val Ser Gln Trp Leu Asn Glu Leu Gln Asp Ala
```

-continued

```
65                  70                  75                  80

Val Asp Ser Ala Glu Asn Leu Met Glu Glu Ile Asn Tyr Glu Val Leu
                85                  90                  95

Arg Leu Lys Val Glu Gly Gln Tyr Gln Asn Leu Gly Glu Thr Ser Asn
            100                 105                 110

Gln Gln Val Ser Asp Leu Asn Leu Cys Leu Ser Asp Glu Phe Phe Leu
        115                 120                 125

Asn Ile Lys Asp Lys Leu Glu Asp Ala Ile Glu Ile Leu Glu Glu Leu
    130                 135                 140

Glu Lys Gln Ile Gly Arg Leu Asp Leu Thr Lys Tyr Leu Asp Ser Asp
145                 150                 155                 160

Lys Gln Glu Thr Arg Arg Leu Ser Thr Ser Val Val Asp Asp Ser Asp
                165                 170                 175

Ile Phe Gly Arg Gln Asn Glu Ile Glu Glu Leu Val Gly Arg Leu Leu
            180                 185                 190

Ser Val Ala Val Asn Gly Lys Asn Leu Thr Val Ile Pro Ile Val Gly
        195                 200                 205

Met Ala Gly Ile Gly Lys Thr Thr Leu Ala Lys Val Val Tyr Asn Asp
    210                 215                 220

Glu Lys Val Lys Asp His Phe Asp Leu Lys Ala Trp Phe Cys Val Ser
225                 230                 235                 240

Glu Pro Tyr Asp Ala Phe Arg Ile Thr Lys Gly Leu Leu Gln Glu Ile
                245                 250                 255

Gly Ser Phe Asp Leu Lys Met Asp Asn Asn Leu Asn Gln Leu Gln Val
            260                 265                 270

Lys Leu Lys Glu Ser Leu Lys Gly Lys Lys Phe Leu Ile Val Leu Asp
        275                 280                 285

Asp Val Trp Asn Asp Asn Tyr Asn Ala Trp Asp Asp Leu Lys Asn Leu
    290                 295                 300

Phe Val Gln Gly Asn Ala Gly Ser Thr Ile Ile Val Thr Thr Arg Lys
305                 310                 315                 320

Lys Ser Val Ala Lys Thr Met Gly Asn Glu Gln Ile Ser Met Asp Thr
                325                 330                 335

Leu Ser Ser Asp Val Ser Trp Ser Leu Phe Lys Arg His Ala Phe Asp
            340                 345                 350

Asn Met Asp Pro Lys Glu His Pro Glu His Val Glu Val Gly Lys Glu
        355                 360                 365

Ile Val Ala Lys Cys Lys Gly Leu Pro Leu Ala Leu Lys Thr Leu Ala
    370                 375                 380

Gly Ile Leu Arg Ser Lys Ser Glu Ile Glu Gly Trp Lys Arg Ile Leu
385                 390                 395                 400

Arg Ser Glu Val Trp Glu Leu Pro Asp Asn Gly Ile Leu Pro Ala Leu
                405                 410                 415

Met Leu Ser Tyr Asn Asp Leu Pro Ala His Leu Lys Gln Cys Phe Ser
            420                 425                 430

Tyr Cys Ala Ile Phe Pro Lys Asp Tyr Pro Phe Arg Lys Lys Gln Val
        435                 440                 445

Ile Gln Leu Trp Ile Ala Asn Gly Leu Val Gln Gly Leu Gln Lys Tyr
    450                 455                 460

Glu Thr Ile Glu Asp Leu Gly Asn Leu Phe Phe Leu Glu Leu Gln Ser
465                 470                 475                 480

Arg Ser Leu Phe Glu Arg Val Pro Glu Ser Ser Lys Asn Asn Ala Glu
                485                 490                 495
```

-continued

```
Lys Phe Leu Met His Asp Leu Val Asn Asp Leu Ala Gln Val Ala Ser
            500                 505                 510

Ser Lys Leu Cys Val Arg Leu Glu Glu Tyr Gln Glu Ser His Met Leu
        515                 520                 525

Lys Arg Ser Arg His Met Ser Tyr Ser Met Gly Tyr Ala Asp Phe Glu
    530                 535                 540

Lys Leu Gln Pro Leu Tyr Lys Leu Glu Gln Leu Arg Thr Leu Leu Pro
545                 550                 555                 560

Ile Tyr Asn Ile Glu Leu Tyr Gly Ser Ser Leu Ser Lys Arg Val Leu
                565                 570                 575

Leu Asn Ile Leu Pro Arg Leu Thr Ser Leu Arg Ala Leu Ser Leu Ser
            580                 585                 590

Arg Tyr Asn Ile Lys Glu Leu Pro Asp Val Leu Phe Ile Lys Leu Lys
        595                 600                 605

Leu Leu Arg Leu Val Asp Leu Ser Leu Thr Gln Ile Ile Gln Leu Pro
    610                 615                 620

Asp Ser Ile Cys Val Leu Tyr Asn Leu Glu Ile Leu Leu Leu Ser Ser
625                 630                 635                 640

Cys Glu Phe Leu Lys Glu Leu Pro Arg Gln Met Glu Lys Leu Ile Asn
                645                 650                 655

Leu Arg His Leu Asp Ile Ser Gly Ser Ser Arg Leu Met Met Pro Leu
            660                 665                 670

His Leu Ser Lys Leu Lys Ser Leu His Val Leu Leu Gly Ala Glu Phe
        675                 680                 685

Leu Val Gly Asp Arg Ser Gly Ser Arg Met Glu Asp Leu Gly Glu Leu
    690                 695                 700

Cys Asn Leu Tyr Gly Thr Leu Ser Ile Arg Gln Leu Glu Asn Val Ala
705                 710                 715                 720

Asp Arg Arg Glu Ala Leu Lys Ala Asn Ile Arg Gly Lys Glu His Ile
                725                 730                 735

Glu Lys Leu Leu Leu Glu Trp Thr Val Ser Ile Ala Asp Ser Ser Gln
            740                 745                 750

Asn Glu Arg Asp Ile Leu Gly Glu Val His Pro Asn Pro Asn Ile Lys
        755                 760                 765

Glu Leu Ala Ile Asn Gly Tyr Arg Gly Thr Asn Phe Pro Asn Trp Leu
    770                 775                 780

Ala Asp Tyr Ser Phe Ser Glu Leu Val Glu Leu Ser Leu Ser Asn Cys
785                 790                 795                 800

Lys Asp Cys Tyr Ser Leu Pro Ala Leu Gly Gln Leu Pro Ser Leu Lys
                805                 810                 815

Phe Leu Ala Ile Arg Gly Thr His Arg Ile Ile Glu Val Thr Glu Glu
            820                 825                 830

Phe Tyr Gly Ser Ser Ser Ser Lys Lys Pro Phe Asn Ser Leu Glu Lys
        835                 840                 845

Leu Asp Phe Ala Glu Met Leu Glu Trp Glu Gln Trp His Val Leu Gly
    850                 855                 860

Asn Gly Glu Phe Pro Val Leu Gln His Leu Ser Ile Glu Asp Cys Pro
865                 870                 875                 880

Lys Leu Ile Gly Lys Leu Pro Glu Asn Leu Cys Ser Leu Thr Lys Leu
                885                 890                 895

Thr Ile Ser His Cys Pro Glu Leu Asn Leu Glu Thr Pro Val Lys Phe
            900                 905                 910
```

-continued

```
Pro Ser Leu Lys Lys Phe Glu Val Glu Gly Ser Pro Lys Ile Gly Val
        915                 920                 925

Leu Phe Asp His Ala Glu Leu Phe Leu Ser Gln Leu Gln Gly Met Lys
    930                 935                 940

Gln Ile Val Glu Leu Tyr Ile Ser Asp Cys His Ser Leu Thr Ser Leu
945                 950                 955                 960

Pro Ile Ser Ser Leu Pro Asn Thr Leu Lys Val Ile Arg Ile Lys His
                965                 970                 975

Cys Glu Lys Leu Lys Leu Glu Ser Ser Val Gly Lys Met Ile Ser Arg
            980                 985                 990

Gly Ser Asn Met Phe Leu Glu Ser  Leu Glu Leu Glu Glu  Cys Asp Ser
        995                 1000                 1005

Ile Asp  Asp Val Ser Pro Glu  Leu Val Pro Cys Ala  Arg Tyr Leu
    1010                 1015                 1020

Arg Val  Glu Asn Cys Leu Ser  Leu Thr Arg Leu Ile  Ile Pro Asn
    1025                 1030                 1035

Gly Ala  Glu Asp Leu Lys Ile  Lys Lys Cys Glu Asn  Leu Glu Ile
    1040                 1045                 1050

Leu Ser  Val Ala Gln Thr Thr  Pro Leu Cys Asn Leu  Leu Ile Ser
    1055                 1060                 1065

Asn Cys  Glu Lys Leu Lys Ser  Leu Pro Glu His Met  Gln Glu Leu
    1070                 1075                 1080

Leu Pro  Ser Leu Arg Asp Leu  Tyr Leu Glu Asn Cys  Ser Glu Ile
    1085                 1090                 1095

Val Ser  Phe Ser Glu Gly Gly  Leu Pro Phe Asn Leu  Glu Ile Leu
    1100                 1105                 1110

Gly Ile  Gln Asp Cys Gly Glu  Leu Val Asn Arg Arg  Lys Glu Trp
    1115                 1120                 1125

Asn Leu  Gln Gly Leu Pro Ser  Leu Thr Tyr Leu Asp  Ile Ile His
    1130                 1135                 1140

Arg Gly  Phe Glu Asn Trp Asp  Ile Ile Cys Glu Leu  Pro Cys Ser
    1145                 1150                 1155

Ile Arg  Ser Leu Thr Ile Asp  Asn Leu Lys Thr Phe  Ser Ser Gln
    1160                 1165                 1170

Val Leu  Lys Ser Leu Thr Ser  Leu Glu Tyr Leu Cys  Thr Ser Asn
    1175                 1180                 1185

Leu Pro  Gln Ile Gln Leu Leu  Leu Glu Glu Gly Leu  Pro Thr Ser
    1190                 1195                 1200

Leu Leu  Met Leu Thr Leu Ser  His His Gly Glu Leu  His Ser Leu
    1205                 1210                 1215

Pro Thr  Asp Gly Leu Arg Arg  Leu Thr Ser Leu Gln  Arg Leu Arg
    1220                 1225                 1230

Ile Asp  Asn Cys Pro Asn Leu  Gln Tyr Val Pro Glu  Ser Thr Phe
    1235                 1240                 1245

Pro Ser  Ser Leu Ser Glu Leu  His Ile Ser Ser Cys  Ser Phe Leu
    1250                 1255                 1260

Gln Ser  Leu Arg Glu Ser Ala  Leu Ser Ser Ser Leu  Ser Asn Leu
    1265                 1270                 1275

Phe Ile  Tyr Thr Cys Pro Asn  Leu Gln Ser Leu Met  Leu Pro Ser
    1280                 1285                 1290

Ser Leu  Phe Glu Leu His Ile  Ile Asp Cys Arg Asn  Leu Gln Ser
    1295                 1300                 1305

Leu Pro  Glu Ser Ala Leu Pro  Pro Ser Leu Ser Lys  Leu Ile Ile
```

-continued

```
    1310                1315                1320

Leu Thr  Cys Pro Asn Leu Gln  Ser Leu Pro Val Lys  Gly Met Pro
    1325                1330                1335

Ser Ser  Ile Ser Phe Leu Ser  Ile Ile Asp Cys Pro  Leu Leu Lys
    1340                1345                1350

Pro Ser  Leu Glu Phe Glu Lys  Gly Glu Tyr Trp Pro  Asn Ile Ala
    1355                1360                1365

His Ile  Pro Thr Ile Val Ile  Asp Cys Glu Cys Leu
    1370                1375                1380


<210> SEQ ID NO 3
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 3

atggagattg gcttagcagt                                              20


<210> SEQ ID NO 4
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 4

tcacaggcat tcacaatcga                                              20


<210> SEQ ID NO 5
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 5

aaaaagcagg ctatgtctta cagtatcact actccatctc                        40


<210> SEQ ID NO 6
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 6

agaaagctgg gttcaagttg caggaccaga gg                                32


<210> SEQ ID NO 7
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 7

aaaaagcagg ctatgtctta caacatcacg agctcg                            36


<210> SEQ ID NO 8
<211> LENGTH: 35
<212> TYPE: DNA
<213> ORGANISM: Artificial Sequence
```

-continued

```
<220> FEATURE:
<223> OTHER INFORMATION: Synthetic Polynucleotide

<400> SEQUENCE: 8

agaaagctgg gtctatgtag ctggcgcagt agtcc                              35


<210> SEQ ID NO 9
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 9

ggggacaagt ttgtacaaaa aagcaggct                                     29


<210> SEQ ID NO 10
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 10

ggggaccact ttgtacaaga aagctgggt                                     29
```